US 8,171,786 B2
May 8, 2012

(12) United States Patent
Burris

(10) Patent No.: US 8,171,786 B2
(45) Date of Patent: May 8, 2012

(54) FUEL INVENTORY MONITORING SYSTEM

(75) Inventor: Steve Y. Burris, Charleston, SC (US)

(73) Assignee: Petroleum Recovery Services, LLC, North Charleston, SC (US)

( * ) Notice: Subject to any disclaimer, the term of this patent is extended or adjusted under 35 U.S.C. 154(b) by 419 days.

(21) Appl. No.: 12/466,610

(22) Filed: May 15, 2009

(65) Prior Publication Data
US 2009/0217753 A1    Sep. 3, 2009

Related U.S. Application Data

(63) Continuation-in-part of application No. 12/274,127, filed on Nov. 19, 2008, now Pat. No. 8,096,177.

(60) Provisional application No. 60/988,916, filed on Nov. 19, 2007.

(51) Int. Cl.
G01F 23/28    (2006.01)
(52) U.S. Cl. ............... 73/290 V; 73/313; 73/309
(58) Field of Classification Search ........... 73/290 V, 73/309, 313, 319
See application file for complete search history.

(56) References Cited

U.S. PATENT DOCUMENTS

| 558,131 | A | 4/1896 | Warren |
|---|---|---|---|
| 781,093 | A | 1/1905 | Post |
| 836,335 | A | 11/1906 | Nichols et al. |
| 1,064,102 | A | 6/1913 | Smith et al. |
| 1,334,007 | A | 3/1920 | White |
| 1,528,003 | A | 3/1925 | Yarnall |
| 1,947,429 | A | 2/1934 | Townsend et al. |
| 2,045,752 | A | 6/1936 | Butterworth |
| 2,116,935 | A | 5/1938 | Richard et al. |
| 2,845,091 | A | 7/1958 | Neer |
| 3,188,238 | A | 6/1965 | Lyon |
| 3,381,709 | A | 5/1968 | Pregno |
| 3,438,215 | A | 4/1969 | Frijlink |
| 3,531,323 | A | 9/1970 | Carpenter et al. |
| 3,747,768 | A | 7/1973 | Barrera |
| 3,797,664 | A | 3/1974 | Pentz et al. |
| 3,825,022 | A | 7/1974 | Metz |
| 4,214,614 | A | 7/1980 | Pyle |
| 4,276,165 | A | 6/1981 | Chamberlain |
| 4,341,232 | A | 7/1982 | Maton |
| 4,537,335 | A | 8/1985 | Rangwala et al. |
| 4,857,185 | A | 8/1989 | Desjardins |
| 5,004,009 | A | 4/1991 | Bunce |
| 5,085,710 | A | 2/1992 | Goss |
| 5,131,271 | A * | 7/1992 | Haynes et al. ............... 73/290 V |
| 5,273,087 | A | 12/1993 | Koch et al. |
| 5,301,702 | A | 4/1994 | McKinney |
| 5,377,729 | A | 1/1995 | Reep |
| 5,585,006 | A | 12/1996 | Jobe |
| 5,603,364 | A | 2/1997 | Kerssies |
| 5,642,743 | A | 7/1997 | Ranes |
| 5,857,716 | A | 1/1999 | Thomas |

(Continued)

Primary Examiner — Hezron E Williams
Assistant Examiner — Rodney T Frank
(74) Attorney, Agent, or Firm — Ryan A. Schneider, Esq.; Troutman Sanders LLP

(57) ABSTRACT

An ultrasonic-based or radar-based apparatus and method for fuel inventory measurements and for the detection and characterization of materials in a fuel tank, including sludge, water, microorganisms and materials of different viscosities and densities that are present in the tank, presented in an easy-to-interpret picture display that can be remotely located from the tank.

18 Claims, 6 Drawing Sheets

U.S. PATENT DOCUMENTS

| | | |
|---|---|---|
| 5,953,287 A | 9/1999 | Willacy et al. |
| 6,213,134 B1 | 4/2001 | Pike |
| 6,298,008 B1 * | 10/2001 | Lyon et al. .................. 367/99 |
| 6,310,830 B1 | 10/2001 | Gruen |
| 6,858,090 B2 | 2/2005 | Hebert |
| 6,915,818 B2 | 7/2005 | Burris et al. |
| 7,264,009 B2 | 9/2007 | Gregory |
| 7,287,425 B2 * | 10/2007 | Lagergren ............... 73/290 V |
| 2004/0173266 A1 | 9/2004 | Burris et al. |
| 2006/0003882 A1 | 1/2006 | Smith |

\* cited by examiner

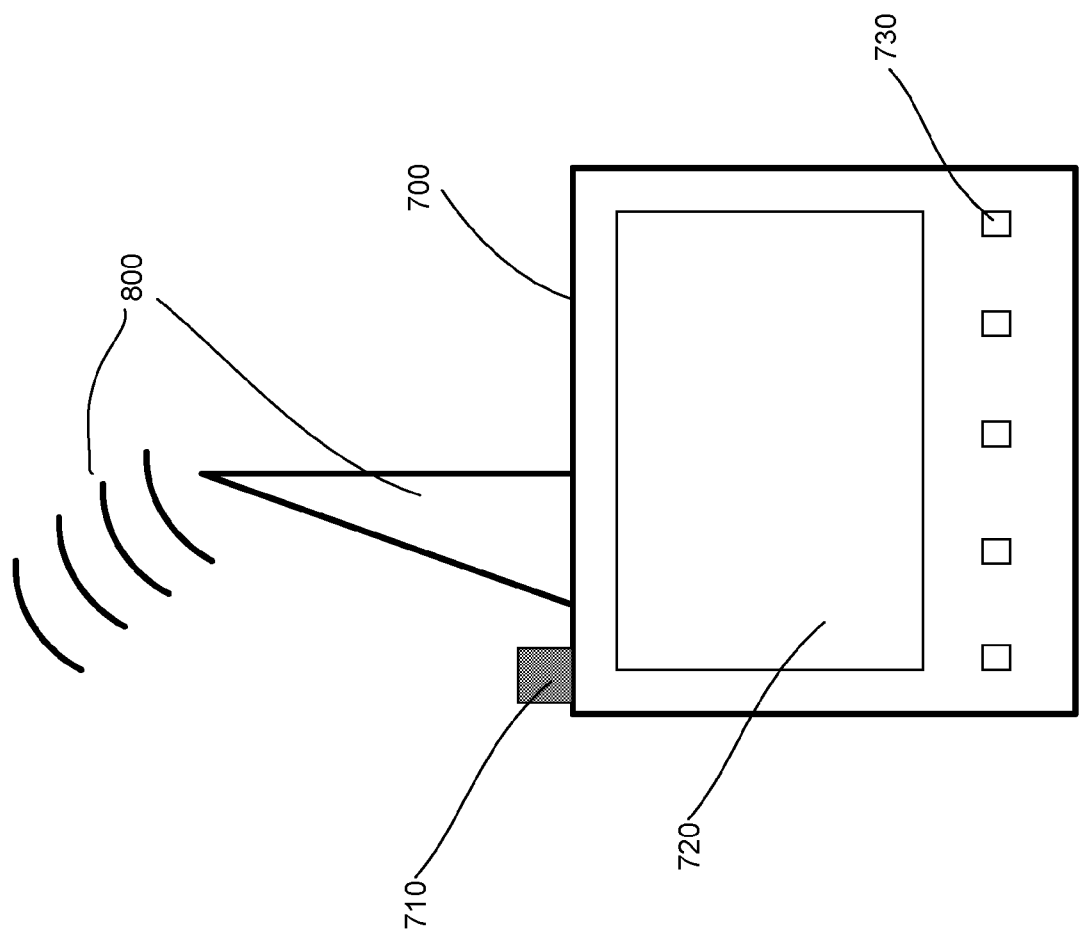

FUEL INVENTORY MONITORING SYSTEM

CROSS REFERENCE TO RELATED APPLICATION AND PRIORITY CLAIM

This patent application claims priority under 35 U.S.C. §120 and is a continuation in part of U.S. Non-Provisional patent application Ser. No. 12/274,127, filed 19 Nov. 2008, and entitled Fuel Inventory Monitoring System, which in turns claims the benefit under 35 U.S.C. §119(e) of U.S. Provisional Patent Application Ser. No. 60/988,916, filed 19 Nov. 2007. Each of the above-listed applications are herein incorporated by reference as if fully set forth below in their entireties

BACKGROUND OF THE INVENTION

1. Field of the Invention

Embodiments of the present invention relate generally to a fuel inventory monitoring system, and more particularly, to an ultrasonic-based or radar-based apparatus and method for the detection and characterization of material in a fuel tank including sludge, water, microorganisms and materials of different viscosities within the tank, the characterization information being presented in an easy-to-interpret picture display for use in determining fuel inventory, leak detection, fuel quality, and the like.

2. Description of Related Art

Current methods for the storage of fuels involve the use of large holding and storage tanks. For purposes of the present description, such tanks are referred to as fuel storage tanks or simply fuel tanks, though other representative applications would include sewage holding and treatment tanks and processing tanks for chemical applications. Such fuel tanks are typically buried underground or are otherwise not easy to access, for maintenance and monitoring applications such as taking an inventory of fuel quantity for determining fuel levels in the tank and for leak detection, and characterizing fuel quality for purposes of facilitating cleaning and removal tasks.

In service-station environments, for example, fuel is delivered to fuel dispensers located at ground level from fuel storage tanks. The fuel storage tanks are often large, cylindrical-shaped containers that may be on the order of 20 meters high and 80 to 100 meters in diameter. Due to regulatory requirements governing service stations, fuel storage tanks are required to be encased in a second or outer casing such that the fuel storage tank contains two walls. These tanks are sometimes referred to as "double-walled tanks." A double-walled tank is comprised of an inner vessel that holds liquid fuel surrounded by an outer casing. A separate fuel storage tank is provided for each fuel type, such as low octane gasoline, high-octane gasoline, and diesel. A pump is used to deliver the fuel from the fuel storage tanks to the fuel dispensers via a main fuel piping conduit that runs beneath the ground in the service station. The fuels contemplated for storage in the tanks include conventional fuels such as gasoline, diesel, and kerosene, as well as newly-developed fuels containing fuel additives such as ethanol and biodiesel.

A common requirement associated with the use of fuel storage tanks is that of sensing or measuring the level of fluid in the tanks, for example, to warn when a tank is full or should be filled, to control the pumping of fluid into or from a tank so as to avoid overflow or pump damage when a tank is empty, and to otherwise control or measure the level of fluid in a tank. Inherent in the process of storing fuel are also known problems that relate to the accuracy of fuel-inventory measurements, generally and retaining fuel quality, in particular. For example, it has long been recognized that the presence of significant amounts of contaminant substances can affect the accuracy of determinations of volume of a fluid from liquid-level measurements. In particular, fuel storage tanks are susceptible to accumulation of water from the delivered product, condensation, damaged fill boxes, bad gaskets, loose fittings and various other non-water/vapor-tight openings.

Contamination of petroleum-based fuels with water has been a commonly encountered difficulty since fuel tanks must be vented to allow replacement of volumes of fuel withdrawn from a tank with the ambient atmosphere in order to avoid developing a partial vacuum in the tank. The ambient atmosphere may be relatively humid, particularly on water-borne vehicles and the temperature differential between the ambient atmosphere and fuel or the fuel tanks (which will often approximate the water temperature) will cause the moisture in the ambient atmosphere to condense to liquid phase. Therefore, substantial quantities of liquid water may accumulate in fuel tanks over a relatively short period of time. Since water has a greater specific gravity than most petroleum fuels, such as diesel fuel, water that enters a fuel tank will generally collect at the bottom of a fuel tank. This leads to the problems of raising the level of the surface of the fuel in the tank, and it causes the water to be trapped at the bottom of the tank since the water generally is non-soluble with the fuel.

Another known recurring problem associated with the sensing or measuring the level of fluid in a tank or other form of container, is that many of the fluids stored in the tank contain or are comprised of substances that leave or form deposits on the inner surfaces of the tank. The deposits themselves may be comprised of solids dissolved or suspended in the fluids or components of the fluids themselves. These deposits, if left untreated, can interfere with or prevent the accurate measurement or detection of the fluid levels.

In the storage of fuel, in particular, it is known that aerobic fungus, bacteria and yeast hydrocarbon utilizing microorganisms will begin to grow at the fuel/water interface. Such sediments will form on the bottom of the tank as the organisms go through life processes. Further, fuel is an organic compound that reacts with air, water, and microbiological growth. It has a relatively short shelf-life and can degrade over time. Thus, when fuel is stored, contaminants often settle out from the fuel. Contaminants that are more dense than the fuel itself generally fall to the bottom of the fuel tank, forming a non-uniform deposit of materials that build up progressively over time and are often referred to collectively as "sludge." Unfortunately, these processes occur where current fuel supply lines are principally located—at the bottom of the tank. As the layers of sludge and water build towards the fuel supply lines, it can artificially inflate the float-level readings which, in turn can lead to erroneous fuel-inventory measurements. Further, if left untreated, the presence of the contaminants can adversely affect the fuel quality. The fuel may even become un-pumpable and non-combustible, which could have catastrophic consequences to the end user.

Currently there are tank-monitoring systems with application to determining fuel-inventory levels, characterizing the topography and/or volume of the layer of sludge in the fuel tank, and defining the location of fluid-water interfaces. Such systems generally employ different methodologies to accomplish the desired result. These include systems for directly measuring the materials in the tank by inserting mechanical devices into the tank to make representative sample measurements, as described in U.S. Pat. No. 5,408,874 to Fleck et al., and as described in U.S. Pat. No. 5,953,287 to Willacy, et al., for example. There are other vibration-based systems that measure the effect of a known applied force to the tank to determine the volume (and/or topography) of the liquids in the tank, for instance, the elastic wave sensing system described in U.S. Pat. No. 5,456,114 to Liu, et al. Other systems include capturing a representative sample of material from the tank and storing the sample in a holding tank for experimentation and characterization, such as that described in U.S. Pat. No. 6,604,408 B2 to Dosramos, et al. Still other systems known in the art include manually lowering a dipstick into the water/sludge layer as well as infrared-based systems that sense temperature gradients within the tank, between the water/sludge and fuel interface, for example, to determine the depth of the water/sludge layer. These are just representative conventional systems used to generally describe the current technology.

There are known problems and limitations encountered with such current systems, however, that limit their effectiveness in many applications. For example, such systems are prone to provide erroneous results when the fuel contains contaminants such as sludge and water. Further, the conventional systems cannot accurately characterize and display the properties of the various contaminants, such as the presence of microorganisms at the fluid-water interface or the formation of crystals from floating fatty acids, which are likely to develop in the fuel storage tank. As a result, such systems are self-limiting in an environment where multiple contaminants are present and the user must be able to quantify the contaminants for improvement of overall fuel quality.

As a typical example of a conventional tank-monitoring system, by way of comparison to the present invention, consider that shown representatively in FIGS. 1a and 1b. Such a system uses mechanical devices inserted into the fuel tank to determine the amount of fuel in the tank by measuring the relative height of the fuel as compared with the water present in the tank. Reference is made to FIG. 1a, which generally depicts such a system 100 with a representation of a cross-sectional view of a cylindrically-shaped fuel tank 200 containing a level of fuel 300 and in which a representative layer of water/sludge 400 has formed at the bottom of the tank 200. This exemplary conventional system comprises an inventory control probe 500 adapted to span from the top to the bottom of the tank 200. The inventory control probe 500 is further adapted to receive a water float 510 and a fuel float 520, and it further comprises means for restraining each float 510, 520 to be in approximate alignment with the vertical axis of the probe 500, but otherwise freely suspended (i.e., floating) in the liquids present in the tank 200. The vertical position of each float 510, 520 can in turn be used to determine the amounts of water 400 and fuel 300 in the fuel tank 200.

The water float 510 is generally located in proximity to the bottom of the probe 500, where the majority of the water 400 will accumulate, and it comprises a rubber boot (not shown) that will float on the water 400, but not the fuel 300. In this way, the water float 510 is generally in contact with the water/fuel interface 410. Sensors in the probe 500 report the vertical position of the water float 510 through a transmitter 600, thus determining the amount of water 400 in the tank 200 based on how high the rubber boot floats on the probe 500.

The fuel float 520 is generally located in proximity near the top of the probe 500, and it comprises a rubber boot (not shown) that is designed to float only on the fuel 300, such that the fuel float 520 is generally located at the fuel/air interface 310. Again, sensors in the probe 500 report the vertical position of the fuel float 520 through the transmitter 600, thus determining the measured inventory as the amount of fuel 300 in the tank 200 based on how high the rubber boot floats on the probe 500. The ullage (empty space or fuel capacity remaining) 320 is determined by subtracting the measured inventory from the charted capacity of the tank 200.

The information from the sensors on the probe can be displayed graphically for the user. Sensors on the probe 500 relay the relative positions of the water float 510 and the fuel float 520, and that positional-information is transmitted to the display console 700 either wirelessly 800, as depicted in FIGS. 1a and 1b, or via cable connections (not depicted, but well understood). The display console 700 is schematically depicted in FIG. 1b. Typical data output from such a system include the relative amounts of water 400 and fuel 300 in the tank 200, the ullage 320, as well as the positions of the fuel/air interface 310 and the water/fuel interface 410. Also, such a system 100 can be used for leak detection by determining the change of inventory in the fuel tank 200 over specific periods during idle time.

Despite their relative simplicity and ease of use, such conventional systems are known to suffer from certain disadvantages. A significant disadvantage commonly encountered is that the probes and floats conventionally used are susceptible to erroneous readings due to sludge that accumulates on the rubber boots and varnish that accumulates on the probe. In particular, because the probes and floats are designed to report the levels of water and fuel, they generally cannot monitor contamination such as sludge, micro organisms or free floating contaminants, and they cannot detect changes in viscosity or density between materials in the fuel. These readings are then reported to the display console in the form of erroneous float-level readings, which in turn results in erroneous determinations of fuel levels. Another significant limitation of such systems is that the information reported to the display console generally does not provide visual references, for example, the relative quantity of the various contaminants as compared with the fuel and water levels in the fuel tank. Such information is essential when it comes to determining fuel quality and for devising clean-up and remedial efforts to improve fuel quality.

Monitoring and maintaining fuel quality is of paramount importance in any fuel-storage application. This has always been the case for conventional fuel systems, such as gasoline and diesel. Further, fuel quality is perhaps the single most important issue faced by alternative fuel producers, distributors and consumers. The importance of such alternative fuels has become crucial in recent years. However, the current storage and distribution infrastructure for handling mineral-based petroleum products was not designed for the dynamics of alternative fuel constituents as they are introduced, substituted and diluted into the system.

As environmental and economic pressures dictate the formulation of our fuels, and alternative fuel sources, in particular, there will be a negative impact on the fuel handling infrastructure that will ultimately adversely affect fuel quality. Because of the demanding requirements on today's fuel delivery systems, particularly injectors, a clean fuel supply is extremely important.

Oxidation, repolymerization, water, microbiological life, waxing, gelling, stratification and separation all have an impact on the storability and operability of fuel. In particular, fuel storage tanks are susceptible to accumulation of water from the delivered product, condensation, damaged fill boxes, bad gaskets, loose fittings and various other non-water/vapor-tight openings. Water is known to be the major cause of contamination in fuels. Whether it is mineral or biodiesel fuel, water adversely affects its quality. It is further recognized that the addition of alcohol in the form of ethanol into gasoline, as well as the addition of methyl esters in the form of biodiesel into diesel, will contribute to the degradation process. Of course, such fuels are susceptible to the sludge build-up and other organic processes, such as described here and elsewhere, which can adversely affect fuel quality. This even assumes that the fuel has a sufficient quality to begin with. Along with these natural degradation processes, fuel may also become contaminated through the distribution chain where it is handled numerous times before it reaches the consumer.

In addition to the foregoing problems that relate to the storage of all fuels, there are certain unique problems that can be associated with the storage of unconventional fuels, such as those with various fuel-additives that are now becoming more often used. These include the addition of ethanol to gasoline and the addition of biodiesel to diesel fuel.

Ethanol, also known as ethyl alcohol, can be blended into gasoline as an alternative fuel or as an octane-boosting, pollution-reducing additive. As an alcohol, ethanol is miscible with water, which means that water and alcohol will completely dissolve into each other.

The problem with storing ethanol-blended gasoline is that if there is water present in the storage vessel, as there inevitably will be as discussed herein, the water will be absorbed into the blend. This absorption will continue until the ethanol/gasoline mixture is saturated with water. At that point, called phase separation, the water/ethanol molecule becomes heavy and will fall out of solution. The result is a distinct layer of gasoline floating on the water/ethanol layer, referred to as separation. This separation occurs at the bottom of the fuel tank where conventional fuel pick-up lines are located. It is thus feasible that an end user (e.g., an engine) could receive a significant quantity of a water/ethanol mixture that is non-combustible and potentially damaging to the engine.

Biodiesel is a fuel comprised of mono-alkyl esters of long chain fatty acids derived from vegetable oils, animal fats or recycled cooking oil, and thus is manufactured from esterified vegetable oil, animal fat or recycled cooking oil. Transesterification is the process of exchanging the alkoxy group of an ester compound by another alcohol. These reactions are often catalyzed by the addition of an acid or base. In this process, the oil is mixed with alcohol in the presence of a hydroxide catalyst to produce biodiesel and glycerin.

Some of the problems associated with biodiesel include the formation of white flakes or sediments at the bottom of the fuel tank that are mostly monoglycerides or saturated fatty acids produced from an incomplete reaction or the improper washing of the fuel. It is also known that crystals can form in biodiesel as the fuel is cooled. These precipitants will plug filters and ultimately can become unpumpable, which again is potentially damaging to the engine.

The primary benefit of biodiesel is that it contains oxygen, so it burns cleaner than ordinary diesel fuel, which contributes to lower levels of particulate-matter emissions. As a mythel ester, biodiesel has solvency characteristics that can also dissolve accumulated sediments. Thus, it will add to the diminished quality of fuel at the bottom of the tank.

Because of the natural degradation processes associated with the handling and the introduction of biomass material into the fuel supply, there will be a need to monitor fuel quality more closely to predict possible problems and formulate potential remedial actions. Therefore, what is needed is a fuel inventory monitoring system that will be able to identify sludge, water, microorganisms, the formation of crystals, free floating fatty acids and changes in viscosity, as well as to determine ullage and changes in inventory for leak detection and inventory control.

There further exists the need for a fuel-inventory system and method that can accurately account for, and differentiate between various contaminants, such as sludge and water, that may be present in the fuel tank. Further, there exists the need for a fuel inventory system and method that can identify and characterize the various contaminants that have developed in the fuel supply, for purposes of determining the best remedial actions needed to improve the fuel quality. In particular, a system can method that can visually depict the various contaminants in the fuel is desirable. It is to such a system and method that the embodiments of the present invention are primarily directed.

SUMMARY OF EXEMPLARY EMBODIMENTS OF THE INVENTION

Embodiments of the present invention relate generally to a fuel inventory monitoring system, and more particularly, to an ultrasonic-based or radar-based apparatus and method for the detection and characterization of material in a fuel tank including sludge, water, microorganisms and materials of different viscosities within the tank, the characterization information being presented in an easy-to-interpret picture display for use in determining fuel inventory, leak detection, fuel quality, and the like. It will be appreciated that the objectives of the present invention may be satisfied by an apparatus and method incorporating a remote sensing system that is either ultrasonic-based (i.e., involving the transmission of sound (sonar) waves) or radar-based (i.e., involving the transmission of electromagnetic (radio or micro) waves). It will further be appreciated that, for some applications, an ultrasonic system may be advantageous since, for example, it is known that sonar waves readily penetrate and travel through water, while other applications may benefit from a radar system since it is known that radar operates at a much higher frequency than sonar and does not require the presence of water or any other particular medium (i.e., can operate in a vacuum). Accordingly, it should be understood that generally when reference is made to a transmitting wave or a reflected/rebounded wave (echo), the embodiments of the present invention contemplate use of a remote sensing system of either type.

Exemplary embodiments of the present invention are therefore directed to a method of, and an apparatus for, the effective detection and characterization of fluid-fluid, fluid-sludge, fluid-solid interfaces using primary transmitted sound energy at either the kilohertz-to-megahertz frequency range (for ultrasonic-based systems) or electromagnetic energy in the gigahertz-to-nanohertz frequency range (for radar-based systems). It is understood that the selection of the specific frequencies for the energy transmission source depends in part upon the actual nature (thickness, attenuation, viscosity, absorption) and distribution properties of the tank walls, as well as the properties of the contaminants and organisms in the fuel tank.

In a preferred embodiment, the invention is an ultrasonic-based or radar-based fuel-inventory detection system comprising a transmitting transducer, a receiving transducer (that may optionally be collocated with the transmitting transducer), a receiver and a display console.

A primary objective of the claimed invention is the accurate and efficient measurement of liquids that are present in the fuel tank for purposes of fuel-inventory management. In order to accomplish the objectives of the invention, with reference to the preferred embodiment, an electrical impulse from the transmitting transducer is converted to a transmitting wave (either a sound wave for ultra-sonic based system, or an electromagnetic (radar or micro) wave for a radar-based system) by the receiving transducer when it is directed towards and sent into a liquid or other object(s) that may be present in the fuel tank. When the transmitting wave strikes an object in its path, the transmitting wave rebounds, creating an echo. This echo strikes the receiving transducer, which receives the echo and converts its energy back into an electrical signal. This electrical signal is amplified by the receiver, and the amplified signal is transmitted to the display console to provide a visual depiction of the object(s) located in the fuel tank.

Preferably, the transmitting transducer may be centrally located on the outer wall at the top of the fuel tank, with an orientation generally directed to the opposing outer wall at the bottom of the fuel tank. Other embodiments are possible, however, with the transmitting transducer capable of being located in other positions on the outside or inside walls of the fuel tank.

Preferably, the receiving transducer may be centrally located on the inner wall at the top of the fuel tank, in proximity to the transmitting transducer and with a similar orientation, so as not to be immersed in the fuel/water mixture present in the tank. Other embodiments are possible, however, with the receiving transducer capable of being located in other positions within the fuel tank. These include a receiving transducer comprising a float device, which is designed to allow the transducer to float on the surface of the fuel. The receiving transducer can also be co-located with the transmitting transducer on the outer wall at the top of the fuel tank, with the understanding that the effects of the tank walls on the transmitted signal would have to be accounted for.

Preferably, the amplified signal is delivered to the display console via a wireless connection, which allows the display console to be remotely located from the fuel tank. Alternatively, the amplified signal can be delivered to the display console via a cabled connection.

An additional objective of the claim invention is to characterize the various contaminants that may have developed in the fuel tank. This objective can effectively be accomplished by recognizing that changes in viscosity, temperature and density will also deflect transmitting waves. Therefore, by using sound or electromagnetic energy in the manner described herein, a visual reference will be created to allow the characterization of changes in the column of fluid. Embodiments of the present system are much more robust in providing visual reference of what is happening in a tank than possible with conventional systems. Embodiments of the present invention detect the distribution and the thickness of sludge, and detect the presence of bulk water, the presence of a microorganism layer at the fluid-fluid (fluid-water) interface, the formation of crystals from the floating fatty acids, and other agglomeration of aggregate materials. Early detection of contamination alerts the fuel users to perform preventative measures.

It is a further objective of the present invention to provide a method of characterizing and quantifying contaminants in a fuel storage tank comprising the steps of creating a transmitting electrical impulse, converting the transmitting electrical impulse to a transmitting (sound or electromagnetic) wave, providing the transmitting wave into the tank, receiving an echo of the transmitting wave (a received wave), converting the echo (received wave) into a received electrical pulse, and transforming the received electrical pulse into a visual reference of the various contaminants.

While sonar and radar are conventionally used in many different applications to provide a visual representation of objects that can not be seen with the naked eye (e.g., ultrasonic sonograms, fish finders, radar detectors, land topography), embodiments of the present invention have a level of tuning not found in the art. Embodiments of the present invention are capable of distinguishing between viscosity and density changes in the fluid, yet such embodiments are robust enough for use within a fuel storage tank.

These and other objects, features and advantages of the embodiments of the present invention will become more apparent upon reading the following specification in conjunction with the accompanying drawings.

BRIEF DESCRIPTION OF THE DRAWINGS

FIG. 2b depicts the display console of the present fuel inventory monitoring system for visually depicting the various contaminants in the fuel storage tank.

DETAILED DESCRIPTION OF THE PREFERRED EMBODIMENTS

Figure 1A:
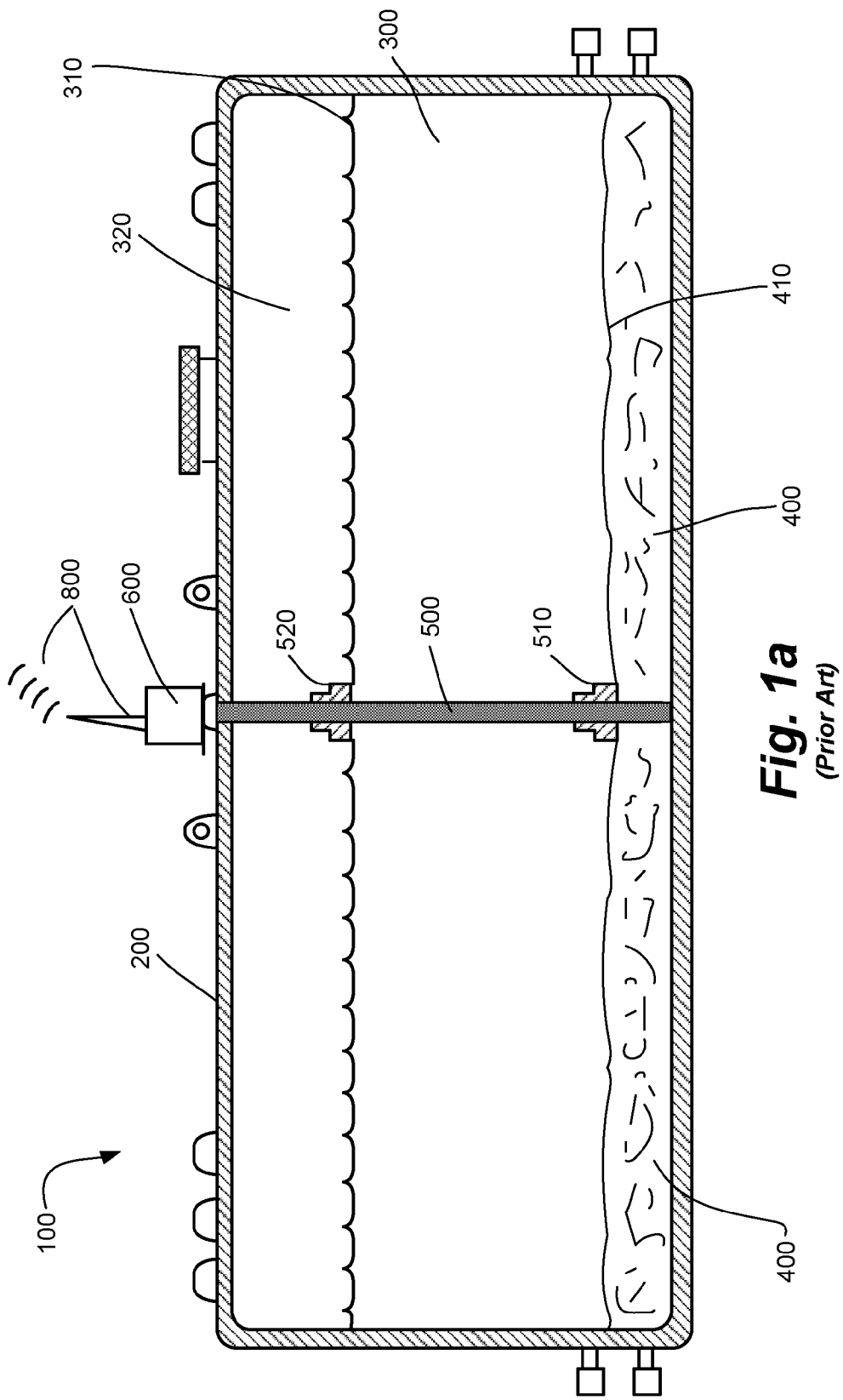
FIG. 1a depicts a cross-sectional view of a cylindrically-shaped fuel storage tank to illustrate a conventional (prior art) fuel inventory monitoring system.
Figure 1B:
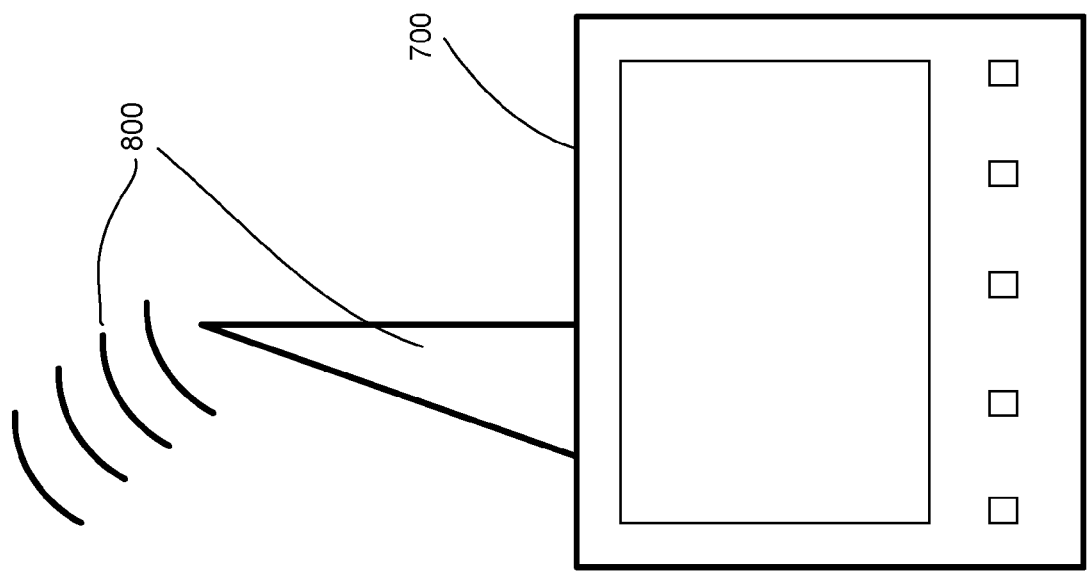
FIG. 1b depicts the display console of a conventional (prior art) fuel inventory monitoring system utilizing a probe and float apparatus.

Referring now in detail to the drawing figures, wherein like reference numerals represent like parts throughout the several views, FIGS. 2a, 2b, 3a and 3b, illustrate preferred embodiments of the present invention being an ultrasonic-based or radar-based detection system that can be used to measure fuel inventory, detect leaks, and quantify contaminants in a fuel storage tank.

In a preferred embodiment, the invention is an ultrasonic-based or radar-based fuel-inventory detection system comprising a transmitting transducer, a receiving transducer, a receiver and a display console. A primary objective of the claimed invention is the accurate and efficient measurement of liquids that are present in the fuel tank for purposes of fuel-inventory management. It will be appreciated that the objectives of the present invention may be satisfied by an apparatus and method incorporating a remote sensing system that is either ultrasonic-based (i.e., involving the transmission of sound (sonar) waves) or radar-based (i.e., involving the transmission of electromagnetic (radio or micro) waves). It will further be appreciated that, for some applications, an ultrasonic system may be advantageous since, for example, it is known that sonar waves readily penetrate and travel through water, while other applications may benefit from a radar system since it is known that radar operates at a much higher frequency than sonar and does not require the presence of water or any other particular medium (i.e., can operate in a vacuum). Accordingly, it should be understood that generally when reference is made to a transmitting wave or a reflected/rebounded wave (echo), the embodiments of the present invention contemplate use of a remote sensing system of either type. Both remote sensing systems perform similar functions, however, since each sends out a series of pulses that are converted to waves (sound waves for an ultrasonic-based system or electromagnetic (radar or micro) waves for a radar-based system) that return as echoes (reflected/rebounded waves) after striking and reflecting/rebounding from certain features or targets so as to allow the determination of important properties and attributes of the target (i.e., shape, size, distribution, density, speed, distance, etc.).

Thus, in order to accomplish the objectives of the invention, with reference to a preferred embodiment, an electrical impulse from the transmitting transducer is converted to a transmitting wave (sound wave for an ultrasonic-based system or electromagnetic (radar or micro-) wave for a radar-based system) by the receiving transducer when it is directed towards and sent into the fuel tank. When the transmitting wave strikes the liquid (fuel, water) that may be present in the tank, the transmitting wave rebounds creating an echo. The speed of propagation of the echo (reflected transmitting wave) is known to vary according to the characteristics of the object(s) from which it rebounds. This echo strikes the receiving transducer, which receives the echo and converts its energy back into an electrical signal. This electrical signal is amplified by the receiver, and the amplified signal is transmitted to the display console to provide a visual depiction of the liquids located in the fuel tank. In this manner, it is possible to provide accurate measurements of fuel inventory levels, determine the ullage, detect for leaks, as well as determine the location of fuel-air and water/fuel interfaces.

It is also possible to accomplish another objective of the present invention, namely, to characterize the contaminants in the fuel tank. This can be accomplished by specifically tuning the transmitting waves (e.g., selection of the appropriate frequency range) to the various materials and contaminants that may be present in the fuel tank, including sludge, water, microorganisms and materials of different viscosities and densities. In this way, changes in viscosity, temperature and density within a volume of fluid can be distinguished and visually depicted to create a snapshot of contaminants present in the fluid.

Figure 2A:
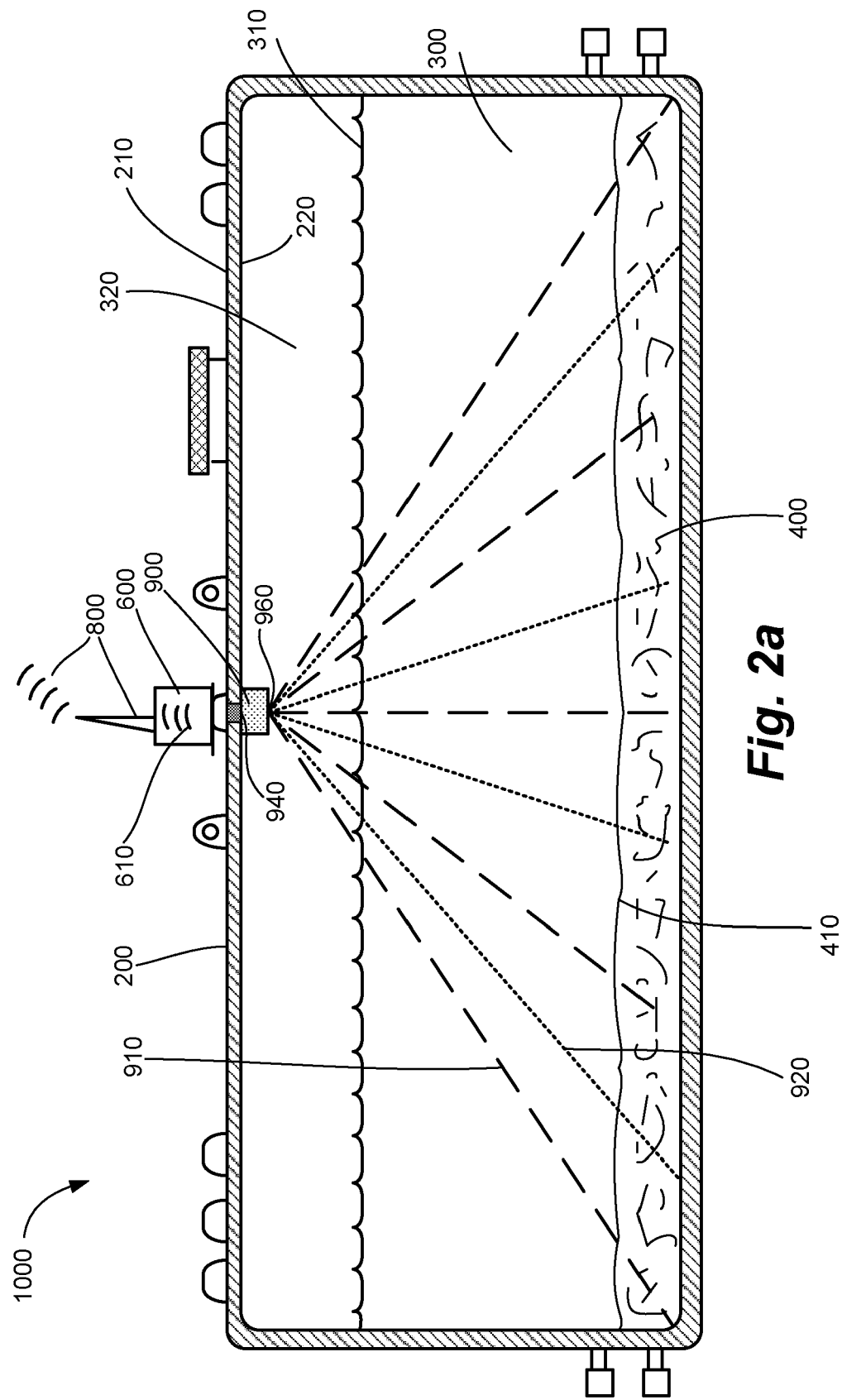
FIG. 2a depicts a cross-sectional view of a cylindrically-shaped fuel storage tank to illustrate the present fuel inventory monitoring system, according to a preferred embodiment for location of the transmitting transducer and the receiving transducer.

With reference to FIG. 2a, a preferred embodiment of the present invention is an ultrasonic-based or radar-based fuel-inventory detection system 1000, which can be used to measure the inventory of fuel 300, detect leaks, and quantify contaminants in a fuel storage tank 200. The tank 200 is depicted in the figures as being cylindrically-shaped, which is a preferable configuration, however, one skilled in the art will recognize that the present invention has application to storage tanks of other shapes and sizes as well. The system comprises a transmitting transducer 600, a receiving transducer 900, a receiver 940, and a display console 700.

As depicted in FIG. 2a, a transmitting electrical impulse 610 from the transmitting transducer 600 is converted to a transmitting wave 910 (sound wave for an ultrasonic-based system or electromagnetic (radar or micro) wave for a radar-based system) by the receiving transducer 900 when the impulse 610 is directed towards and sent into a liquid (fuel 300 and/or water 400) that may be present in the fuel tank 200. When the transmitting wave 910 strikes the various contaminants in the tank 200, the transmitting wave 910 rebounds, creating an echo (a reflected wave) 920. This echo 920 strikes the receiving transducer 900, which receives the echo 920 and converts its energy back into a received electrical signal 960. This received electrical signal 960 is amplified by the receiver 940 in communication with the receiving transducer 900, and the amplified signal is transmitted 800 to the display console 700, as schematically depicted in FIG. 2b. This provides a visual depiction of the object(s) located in the fuel tank 200.

By transmitting and displaying the echo 920 many times per second (i.e., using a high sample rate), a continuous line is produced to describe the contours of objects between the bottom of the tank 200 and the receiving transducer 900. In this manner, it is possible to characterize the contaminants in the fuel tank including sludge, water, microorganisms and materials of different viscosities.

Embodiments of the present invention can position the transmitting transducer 600 in numerous beneficial locations. Preferably, the transmitting transducer 600 is centrally located on an outer wall 210 of a top of the fuel tank 200, as depicted in FIG. 2a, such that a vertical axis of the transmitting transducer 600 is generally oriented and directed to an opposing outer wall at a bottom of the fuel tank 200. In this manner, the transmitting electrical impulse 610 can be transmitted through the walls of the tank 200. Other embodiments are possible (not depicted), however, with the transmitting transducer 600 being located in other positions on the outer wall 210 or inner wall 220 of the fuel tank 200 at the convenience of the user.

Embodiments of the present invention can locate the receiving transducer in numerous beneficial locations. Preferably, the receiving transducer 900 is centrally located at an inner wall 220 of the top of the fuel tank 200, in close proximity to the transmitting transducer 600 and with a similar orientation, such that a vertical axis of the receiving transducer 900 is generally oriented and directed to the opposing outer wall 210 at the bottom of the fuel tank 200, as depicted in FIG. 2a. In this manner, the transmitting electrical impulse 610 can be sensed by the receiving transducer 900 as it is transmitted through the walls of the tank 200. Assuming the fuel tank 200 is not filled to capacity, there will be a portion of air through which the transmitting wave 910 and the reflected wave 920 must travel as the waves pass to and from the receiving transducer 900 to the object being sensed (and then on return from the object being sensed to the receiving transducer 900). Therefore, it is necessary to account for the speed of the waves traveling though the air.

The system can be calibrated to detect, for example, changes in the characteristics of the transmitting waves according to the medium present in the fuel tank and in the vicinity of the propagation path of the transmitting waves. So, by way of example only, consider the use of an ultrasonic-based system with a fuel tank partially filled with water and with the receiving transducer located at a fixed position at the top of the tank shooting downward. Then the transmitting wave will be a sound wave that has to travel through the air, and then through the water where it will be deflected back by the bottom of the tank. It is known that the speed of sound in water exceeds that in air by a factor of approximately 4.4, so a calculation is required to differentiate between the water and the air.

Figure 3A:
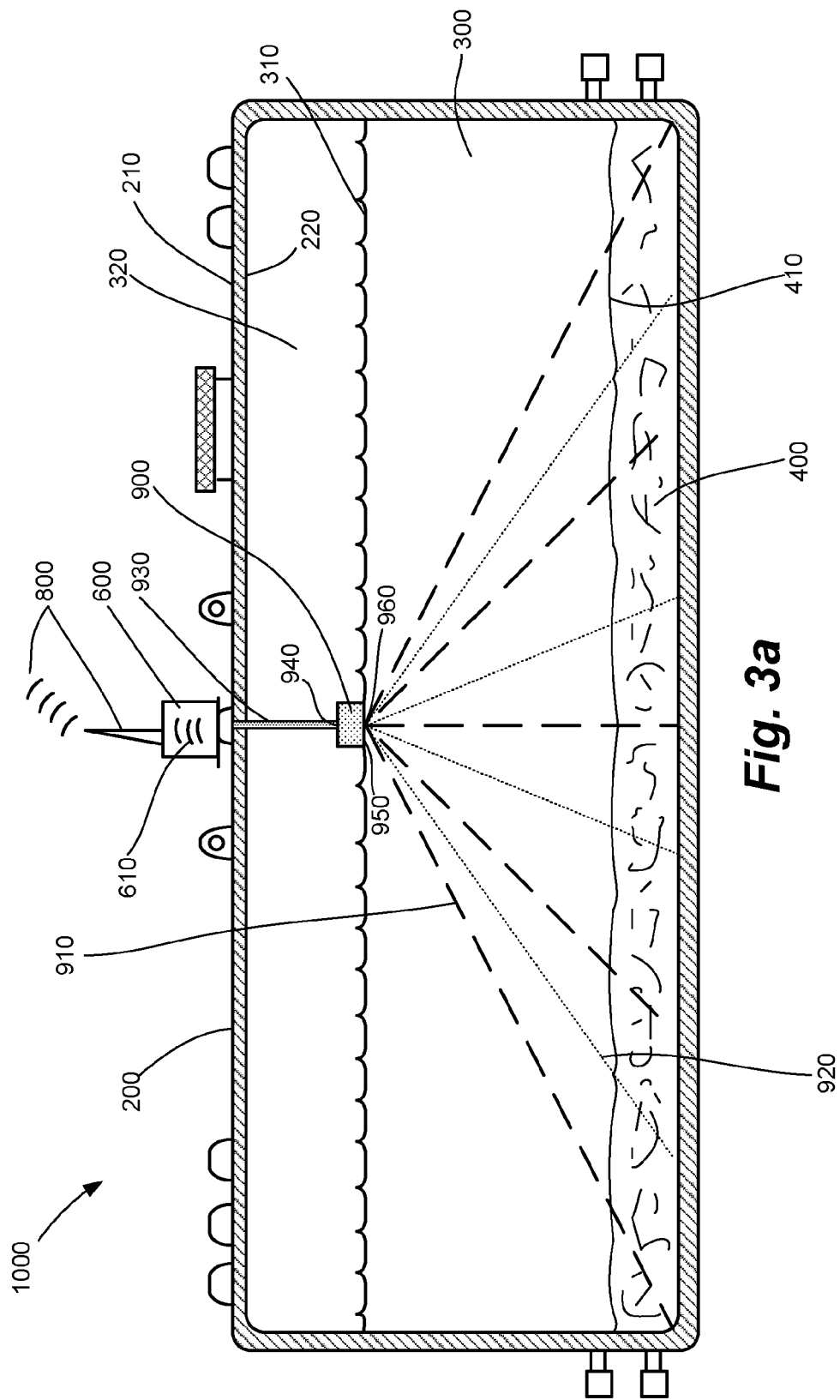
FIG. 3a depicts a cross-sectional view of a cylindrically-shaped fuel storage tank to illustrate the present fuel inventory monitoring system, according to another preferred embodiment for location of the transmitting transducer and the receiving transducer.
Figure 3B:
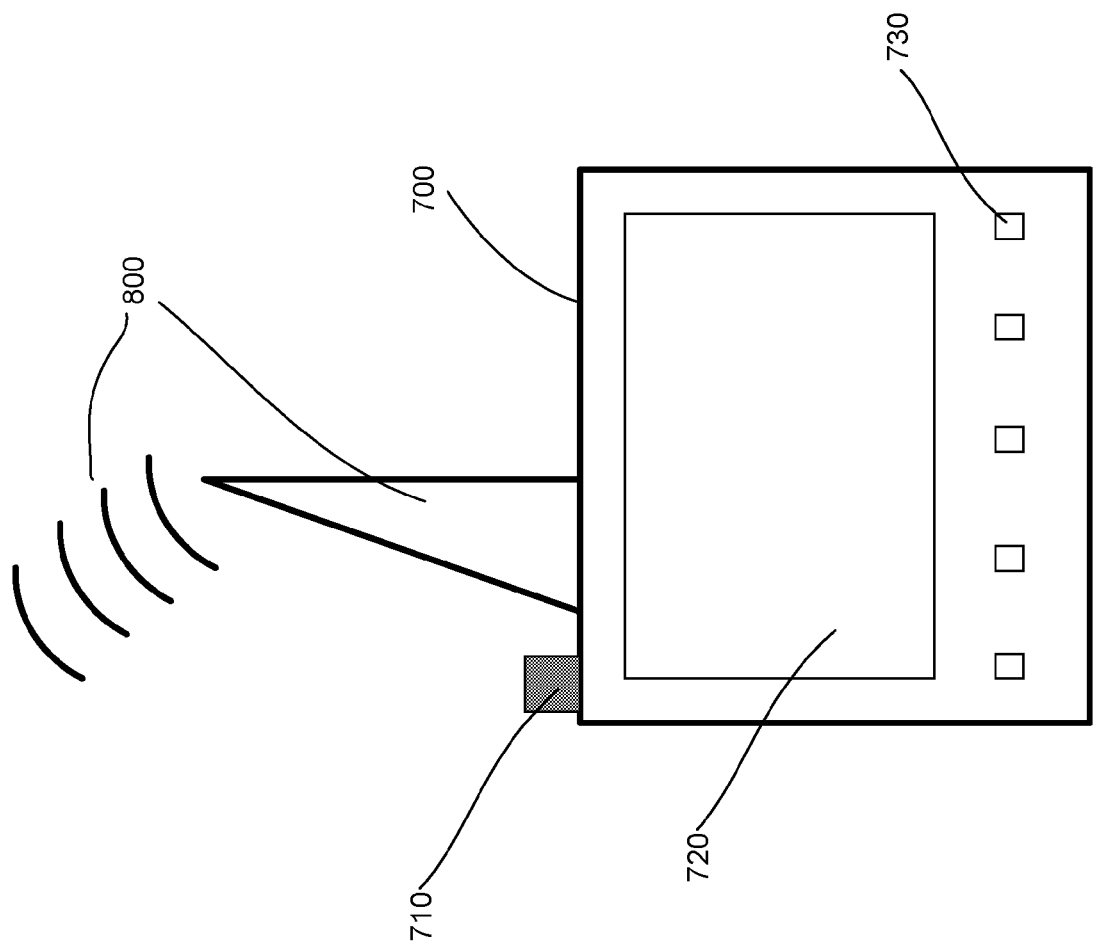
FIG. 3b depicts the display console of the present fuel inventory monitoring system for visually depicting the various contaminants in the fuel storage tank.

The foregoing difficulty can also be compensated for, by way of example only, by placing the receiving transducer 900 at other locations within the fuel tank 200. One such arrangement is schematically depicted in FIG. 3a. The receiving transducer 900 is adapted to receive a float device 950, which can be collocated with the receiving transducer 900, with means for restraining the float device 950 to be in approximate alignment with the vertical axis of the transmitting transducer 600 and the receiving transducer 900, but otherwise freely suspended (i.e., floating) in the liquids present in the tank 200. This allows the receiving transducer 900 to float on the surface of the fuel 300 at the fuel/air interface 310. Such an arrangement avoids the need to account for variance in the propagation speed of the transmitting wave 910 and the reflected wave (echo) 920 between the transmitting transducer 600 and the receiving transducer 900. In another preferred embodiment (not depicted), the receiving transducer 900 can be submerged on the bottom of the tank 200, e.g., floating at the water level, and it can be directed to sense and reflect the electrical impulse upwards. In yet another preferred embodiment (not depicted), the receiving transducer 900 can be located outside of the fuel storage tank 200, with the understanding that the effects of the walls of the tank 200 on the transmitting electrical impulse 610 and the received electrical signal 960 are accounted for. The communication 800 between the receiving transducer 900 and the display console 700, schematically depicted in FIGS. 2b and 3b, is essentially the same no matter where the receiving transducer 900 is located.

With further reference to FIG. 2a, by way of example, various materials present in the fuel tank 200 can be characterized by the present invention. These include the water and sludge mixture 400, the water/sludge interface layer 410 (which is composed of micro organisms), the fuel 300 and the accompanying fuel-air interface 310, as well as changes in viscosity, changes in temperature and the presence of hard fixtures (such as pick-up lines, submersible pumps). The visual representation of these various materials is based on the echo strength of the object being sensed as determined by the receiver 940, which in a preferred embodiment can further measure the strength of the echo. By transmitting and displaying the echo 920 many times per second (i.e., using a high sample rate), a continuous line will be produced to describe the contours of an object between the bottom of the tank 200 and the receiving transducer 900. In this manner, it is possible to characterize the contaminants in the fuel tank including sludge, water, microorganisms and materials of different viscosities. The monitor on the display console 700 is also programmed to provide additional information, such as temperature and temperature gradients and inventory levels.

Embodiments of the present invention can detect the distribution and the thickness of sludge 400 that has settled at the bottom of the tank 200. The invention can also detect the presence of bulk water 400, the presence of a microorganism layer at the fluid-fluid (fluid-water) interface, the formation of crystals from floating fatty acids, as well as other agglomeration of aggregate material.

In a preferred embodiment, the receiving transducer is tuned to specific frequencies and wave lengths to discern between fluid-fluid, fluid-sludge, fluid-solid interfaces using primary transmitted sound energy at either the kilohertz-to-megahertz frequency range (for ultrasonic-based systems) or electromagnetic energy in the gigahertz-to-nanohertz frequency range (for radar-based systems). It is understood that the selection of the specific frequencies for the energy transmission source depends upon the actual nature (thickness, attenuation, viscosity, absorption) and distribution properties of the tank walls, the liquids in the tank (fuel and water), as well as the properties of the contaminants and organisms themselves. Precise calibration of both the transmitting and receiving waves and associated energies is generally required. Preferably, the energies needed may range from hundreds of kilohertz up to the megahertz range for an ultrasonic-based system, and much higher (up to the nanohertz range) for a radar-based system, to properly detect wave distortion, echo energy loss and time of flight in the data acquisition and processing of signals.

Preferably, the amplified signal is delivered to the display console 700 via a wireless connection 800, which allows the display console 700 to be remotely located from the fuel tank 200. Alternatively, the amplified signal can be delivered to the display console 700 via a cabled connection (not depicted, but well understood how to accomplish this connection). The display console 700 also can communicate via a modem (not depicted) so it can be remotely accessed.

The display console 700 is schematically depicted in FIGS. 2b and 3b. The display console can include a numeric-pad for data entry, an LED screen, a roll printer, alarm lights and audio alarms. Data output from such the present system includes the relative amounts of water 400 and fuel 300 in the tank 200, the ullage 320, as well as the positions of the fuel-air interface 310 and the water/sludge-fuel interface 410, as depicted in FIGS. 2a and 3a. Also, such a system 1000 can be used for leak detection by determining the change of inventory in the fuel tank 200 over specific periods during idle time.

The display console 700 of a preferred embodiment of the present invention has capabilities beyond that currently available. The display console 700 is preferably solar powered 710, but can be run on conventional sources of electricity, including standard line or battery. The display console 700 also includes a monitor 720 that prints the echo many times per second, so a continuous line is drawn across the monitor 720 to visually depict the contour of an object between the bottom of the tank 200 and the transmitting transducer 600. The display console 700 and monitor 720 are adapted to incorporate a touch-screen keypad 730 to allow the user to conveniently obtain one-touch information, such as, but not limited to: tank volume, inventory, ullage, temperature, water level, zoom, leak detection, viscosity, and particulate identification.

Embodiments of the present invention further comprise a method of characterizing and quantifying contaminants in a fuel storage tank. This method, in a preferred embodiment, comprises the steps of creating a transmitting electrical impulse 610, converting the transmitting electrical impulse 610 into a transmitting wave 910 (sound wave for an ultrasonic-based system or electromagnetic (radar or micro) wave for a radar-based system), providing the transmitting wave 910 into the tank 200, receiving an echo of the transmitting wave (a reflected wave) 920, converting the echo (reflected wave) 920 into a received electrical signal 960, and transforming the received electrical signal 960 into a visual reference of the various contaminants in the tank 200.

One embodiment of the present method is described by way of reference to FIG. 2a, however, it is understood that the description also applies to the system depicted in FIG. 3a, with the exception of the location of the receiving transducer 900 that varies between the two schematic depictions. Preferably, the step of creating the transmitting electrical impulse 610 is accomplished by way of a transmitting transducer 600, which can be mounted on the outer wall 210 at the top of the tank 200, as depicted in FIG. 2a. In this position, a vertical axis of the transmitting transducer 600 is generally oriented and directed to an opposing outer wall 210 at a bottom of the fuel tank 200. In this manner, the transmitting electrical impulse 610 can be transmitted through the walls of the tank 200. The transmitting transducer 600 can also be positioned in other locations as well (not depicted).

Preferably, the step of converting the transmitting electrical impulse 600 into a transmitting wave 910 is accomplished by way of a receiving transducer 900, which may be mounted on the inner face of the wall 220 of the tank 200, or which may be designed to float 950 at the fuel/air interface 310, as depicted in FIGS. 2a and 3a, respectively. In either case, the receiving transducer 600 is generally oriented in fashion similar to the transmitting transducer 900, with its vertical axis directed to the opposing outer wall 210 at the bottom of the fuel tank 200. In this manner, the transmitting electrical impulse 610 can be sensed by the receiving transducer 900 as it is transmitted through the walls of the tank 200. The transmitting transducer 600 may be positioned in other locations as well (not depicted), such as being submerged at the water/fuel interface 410.

Preferably, the steps of receiving an echo of the transmitting wave 920 and converting the echo 920 into a received electrical signal 960 may be accomplished by way of a receiver 940 that is in communication with the receiving transducer 900.

Preferably, the step of transforming the received electrical signal 960 into a visual reference of the various contaminants is accomplished by way of wireless communication 800 of the received electrical signal 960 to the display console 700 for visual display of the materials and contaminants present in the fuel tank 200. In this manner, it is possible to characterize the contaminants in the fuel tank 200 including sludge, water, microorganisms and materials of different viscosities. The communication between the receiving transducer 900 and the display console 700 can also be accomplished by cable connections (not depicted, but well understood how to accomplish this).

Further embodiments of the present invention can further comprise sonication equipment to use ultrasonic (sound) wave pulses to break up and disperse the contaminants that may be present in the fuel.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A remote-sensing fuel inventory monitoring system, capable of measuring fuel levels and detecting and characterizing water and other contaminants in fuel storage tanks, comprising:
    a transmitting transducer for transmitting an electrical impulse into a tank;
    a receiving transducer for converting the transmitting electrical impulse into a transmitting wave and for converting an echo of the transmitting wave into a received electrical signal, the receiving transducer comprising a buoyant float device;
    a receiver for amplifying and transmitting the received electrical signal, the receiver measuring a change of strength of the echo; and
    a display console for receiving the received electrical signal, and displaying the received electrical signal as a visual depiction of the contents in the tank;
    wherein the echo strength is measured with a frequency sufficient to detect the presence of materials of differing viscosities and densities in the tank.

2. The remote-sensing fuel inventory monitoring system of claim 1,
    wherein the transmitting transducer is located on an outer face of a wall of the tank, and
    wherein a vertical axis of the transmitting transducer is generally oriented to be perpendicular with the wall of the tank such that the transmitting electrical impulse travels through the wall of the tank.

3. The remote-sensing fuel inventory monitoring system of claim 2,
    wherein the receiving transducer is located on an inner face of the wall of the tank, and
    wherein a vertical axis of the receiving transducer is generally oriented to be in approximate alignment with the vertical axis of the transmitting transducer to direct the transmitting sound wave toward an inner face of an opposing wall of the tank.

4. The remote-sensing fuel inventory monitoring system of claim 2,
    wherein the transmitting wave is tuned to be in the sound wave frequency range.

5. The remote-sensing fuel inventory monitoring system of claim 1,
    wherein the transmitting wave is tuned to be in the electromagnetic wave frequency range.

6. The remote-sensing fuel inventory monitoring system of claim 2,
    wherein the receiving transducer is in approximate alignment with the vertical axis of the transmitting transducer for positioning the receiving transducer at a fuel-air interface.

7. The remote-sensing fuel inventory monitoring system of claim 1,
    wherein the received electrical signal is transmitted wirelessly to the display console, and
    wherein the display console is located remotely from the tank.

8. The remote-sensing fuel inventory monitoring system of claim 1,
    wherein the display console further comprises a solar-power source and a touch-screen keypad to provide one-touch visual representation of water or contaminants within the tank.

9. The remote-sensing fuel inventory monitoring system of claim 8,
    wherein the properties displayed comprise tank volume, tank inventory, ullage, temperature, water level, leak detection, viscosity and contaminate identification.

10. A remote-sensing fuel inventory monitoring system, capable of measuring fuel levels and detecting and characterizing water and other contaminants in fuel storage tanks, comprising:
    a transmitting transducer located on an outer face of a wall of the tank for transmitting an electrical impulse through the wall and into the tank;
    a receiving transducer located on an inner face of the wall of the tank for converting the transmitting electrical impulse into a transmitting wave and for converting an echo of the transmitting wave into a received electrical signal, the receiving transducer comprising a buoyant float device;
    a receiver for amplifying and transmitting the received electrical signal, the receiver measuring a change of strength of the echo; and
    a display console for receiving the received electrical signal and for displaying the received electrical signal as a visual depiction of the contents in the tank,
    wherein a vertical axis of the transmitting transducer is generally oriented to be perpendicular with the wall of the tank,
    wherein a vertical axis of the receiving transducer is generally oriented to be in approximate alignment with the vertical axis of the transmitting transducer to direct the transmitting sound wave toward an inner face of an opposing wall of the tank, and wherein the echo strength is measured with a frequency sufficient to detect the presence of materials of differing viscosities and densities in the tank.

11. The remote-sensing fuel inventory monitoring system of claim 10,
wherein the transmitting wave is tuned to be in the sound wave frequency range.

12. The remote-sensing fuel inventory monitoring system of claim 10,
wherein the transmitting wave is tuned to be in the electromagnetic wave frequency range.

13. A method of fuel inventory monitoring capable of remotely sensing and measuring fuel levels and characterizing and quantifying water and other contaminants in a fuel storage tank, comprising the steps of:
creating a transmitting electrical impulse;
converting the transmitting electrical impulse into a transmitting wave;
providing the transmitting wave into the tank;
receiving an echo of the transmitting wave with a receiving transducer comprising a buoyant float device;
measuring the echo strength by converting the echo into a received electrical signal; and
transforming the received electrical signal into a visual reference of any water or contaminants in the tank by measuring the echo strength with a frequency sufficient to detect the presence of materials of differing viscosities and densities in the tank.

14. The method of claim 13, wherein the steps of creating and converting the transmitting electrical impulse comprise providing a transmitting transducer located on an outer face of a wall of the tank, with a vertical axis of the transmitting transducer generally oriented to be perpendicular with the wall of the tank.

15. The method of claim 14, wherein the steps of providing the transmitting wave into the tank and receiving the echo comprise providing a receiving transducer located on an inner face of the wall of the tank, with a vertical axis of the receiving transducer generally oriented to be in approximate alignment with the vertical axis of the transmitting transducer to direct the transmitting wave toward an inner face of an opposing wall of the tank.

16. The method of claim 14, wherein the receiving transducer is in approximate alignment with the vertical axis of the transmitting transducer for positioning the receiving transducer at a fuel-air interface.

17. The method of claim 13, wherein the step of converting the transmitting electrical impulse into a transmitting wave comprises tuning the transmitting wave to be in the sound wave frequency range.

18. The method of claim 13, wherein the step of converting the transmitting electrical impulse into a transmitting wave comprises tuning the transmitting wave to be in the electromagnetic wave frequency range.

* * * * *